(12) United States Patent
Yvin et al.

(10) Patent No.: US 7,070,778 B2
(45) Date of Patent: Jul. 4, 2006

(54) THERAPEUTICAL COMBINATION AGAINST CANCER

(75) Inventors: Jean-Claude Yvin, Saint Malo (FR); Edouard Panak, Toulouse (FR); Vaclav Vetvicka, Louisville, KY (US)

(73) Assignee: Laboratoire Goemar SA, Saint-Malo (FR)

( * ) Notice: Subject to any disclaimer, the term of this patent is extended or adjusted under 35 U.S.C. 154(b) by 126 days.

(21) Appl. No.: 10/698,034

(22) Filed: Oct. 30, 2003

(65) Prior Publication Data

US 2005/0095250 A1 May 5, 2005

(51) Int. Cl.
*A61K 39/395* (2006.01)
*A61K 31/715* (2006.01)
*A01N 43/04* (2006.01)

(52) U.S. Cl. .............................. 424/155.1; 424/143.1; 424/180.1; 424/181.1; 514/54; 514/61

(58) Field of Classification Search .................. 514/54, 514/61; 424/130.1, 141.1, 143.1, 180.1, 424/181.1, 155.1
See application file for complete search history.

(56) References Cited

U.S. PATENT DOCUMENTS 6,632,940 B1  10/2003  Yvin et al.

2003/0045706 A1  3/2003  Yvin et al.

FOREIGN PATENT DOCUMENTS

| WO | WO 98/39013 | 9/1998 | |
|---|---|---|---|
| WO | WO 02/05871 A1 * | 8/2002 | ............... 514/54 |
| WO | WO 03-045414 | 6/2003 | |

OTHER PUBLICATIONS

Bohn et al. (Carbohydrate Polymers, 28, Mar. 14, 1995).*
Gura (Science, v278, 1997, pp. 1041-1042).*
Tschmelitsch et al. (Canc. Res., 1997, vol. 57, No. 11, abstract).*
Anishi et al., "Induction of TNF-α Production from Human Peripheral Blood Monocytes with β-1,3-Glucan Oligomer Prepared from Laminarin...", Journal of Bioscience and BioEngineering, vol. 95, No. 2, pp. 192-195, 2003.

* cited by examiner

*Primary Examiner*—Jeffrey Siew
*Assistant Examiner*—Brandon Fetterolf
(74) *Attorney, Agent, or Firm*—Stites & Harbison PLLC; B. Aaron Schulman

(57) ABSTRACT

The present invention relates to compositions and methods for treating humans and warm-blood animals suffering from cancer. More particularly, a therapeutical treatment in which a monoclonal antibody is administered with either β-(1,3)-glucan like laminarin or a oligo-β-(1,3)-glucan and a pharmaceutically acceptable carrier, to patients suffering from cancer are described.

9 Claims, 1 Drawing Sheet

THERAPEUTICAL COMBINATION AGAINST CANCER

The present invention relates to a therapeutical treatment in which a monoclonal antibody is administered with either β-(1,3)-glucan like laminarin or a oligo-β-(1,3)-glucan to patients suffering from cancer and to drugs used in said treatment.

More particularly, it relates to a method of treatment of humans and warm-blood animals suffering from cancer.

Glucans which are natural products have been studied extensively and are known as presenting immunostimulating activities. However, it has already been observed that not every compound comprised into naturally occurring glucans are active.

Among the already studied glucans, laminarin can be cited as presenting immunostimulant activities and consequently as being useful in therapeutical treatments, in particular for patient suffering from cancer, as disclosed e.g. in the International patent application WO03/045414 in the name of the present inventors.

Furthermore, the Applicants have also found that some of specific oligo-β-(1,3)-glucans also present an immunostimulating activity. Those oligo-β-(1,3)-glucans are those presenting the following formula:

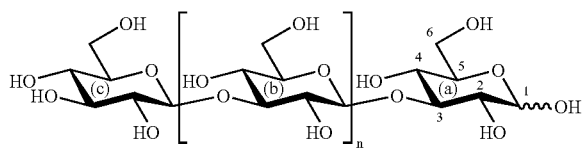

in which n=1 to 10, preferably, n=2 or n=3, or a pharmaceutically acceptable salt thereof.

Monoclonal antibodies are typically made by fusing a normally short-lived, antibody-producing B cell (see immunity) to a fast-growing cell, such as a cancer cell (sometimes referred to as an "immortal" cell). The resulting hybrid cell, or hybridoma, multiplies rapidly, creating a clone that produces large quantities of the antibody. Monoclonal antibodies engendered much excitement in the medical world in the 1980's, especially as potential cures for cancer.

In order to use these antibodies in treatments against cancer, the searchers need to find antigens on the surface of cancer cells which were found only on those cancer cells and were not found on normal tissues, and then produce monoclonal antibodies to those antigens.

The theory is that these monoclonal antibodies could then recognize the antigen on the cancer cells and lock on to it (like a key in a lock). This might then trigger the body's immune system to attack the cancer cells. Alternatively the monoclonal antibody could have a cancer drug or a radioactive substance attached to it and be used to deliver treatment directly to the cancer (this was called targeted therapy or the "magic bullet").

In the last twenty five years a great deal of research has gone into both looking for antigens on cancer cells and improving production of monoclonal antibodies so that the large quantities necessary for medical use could be made.

However the demand for treatments against cancer which are very effective and not harmful continues to exist.

Surprisingly and unexpectedly, the present inventors found that monoclonal antibody and either β-(1,3)-glucan like Laminarin or oligo-β-(1,3)-glucan has a synergistic effect on the treatment of cancer.

The present invention is based on said synergistic effect.

An object of the present invention is thus a therapeutical method comprising administration of a composition comprising a monoclonal antibody with either a β-(1,3)-glucan like laminarin or an oligo-β-(1,3)-glucan and a pharmaceutically acceptable carrier, to a human being or to a warm-blood animal suffering from cancer in an amount which is effective to treat the cancer.

Throughout the specification the amount of active composition is considered as "effective" if it allows the obtention of the contemplated medical end such as control or destruction of cancer cells without producing unacceptable toxic symptoms. Said effective amount will vary with factors such as the particular condition being treated, the physical condition of the patients and the duration of the treatment.

The "pharmaceutical acceptable carrier" is selected from the group comprising pharmaceutically acceptable solvents, suspending agents or vehicles, and in function of the chosen route selected for administration, and keeping in mind standard pharmaceutical practice; "acceptable" means that the carrier is compatible with the other ingredients of the formulation and not injurious to the patient.

More generally, a "pharmaceutically acceptable component" should not present or induce undue adverse side effects such as toxicity, irritation, and allergic response and should be commensurate with a reasonable benefit/risk ratio.

Laminarin is a naturally occurring glucan which is extracted from brown algae and which consists in polysaccharides with an average molecular weight between about 2,500 to 6,000.

A commercially available laminarin is marketed by the Assignee for other purposes.

The oligo-β-(1,3)-glucan is a compound presenting the following formula (1):

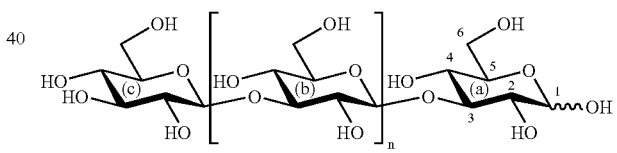

in which n=1 to 10, preferably, n=2 or 3, or a pharmaceutically acceptable salt thereof.

Advantageously, the active oligo-β-(1,3)-glucans are those of Formula I above, in which n=2, i.e. β-D-glucopyranosyl-(1→3)-β-D-glucopyranosyl-(1→3)-β-D-glucopyranosyl-(1→3)-β-D-glucopyranose, which is called Laminaritetraose, or in which n=3, i.e. the β-D-glucopyranosyl-(1→3)-β-D-glucopyranosyl-(1→3)-β-D-glucopyranosyl-(1→3)-β-D-glucopyranosyl-(1→3)-β-D-glucopyranose, which is called Laminaripentaose.

Those compounds can be synthesized by deprotection and purification of the compounds prepared according to the process disclosed in WO01/57053 in the name of the Assignee. Methods of de-protection and purification usable are described with reference to laminaribiose in FR2777281.

In the method according to the invention, the monoclonal antibody is any monoclonal antibody specific to molecular determinants present on cancer cells and simultaneously able to activate complement.

Advantageously, the monoclonal antibody is selected from the group comprising Herceptin, Alemtuzumab, Rituximab, Tositumomab, Campath, Cetuximab (Erbitux®), Edrecolomab, Mylotarg, Panorex, Pentumomab.

The method according to the invention is suitable to treat cancer, specifically, leukemia, adenocarcinoma, breast cancer, lung cancer, ovarian cancer, oesophagus cancer, stomach cancer, intestinal cancer, non-Hodgkin lymphoma or colon cancer.

Since the monoclonal antibody is administered with either a β-(1,3)-glucan like Laminarin or an oligo-β-(1,3)-glucan, the therapy can be called "combination therapy".

Combination therapy can be sequential, which means that the treatment is carried out with one agent first and then with the second agent; or it can be simultaneous, which means that both agents are administered at the same time.

In the method according to the invention, the effective amount of either β-(1,3)-glucan like Laminarin or oligo-β-(1,3)-glucan is 2 to 20 mg/kg when administered orally for a sequential treatment. The amount of monoclonal antibody is the conventional amount used in treatment of cancers.

According to another object of the invention, the method according to the invention further comprises administration of a chemotherapeutic agent for an enhanced potentiation.

The present invention also relates to the compositions useful in the above mentioned therapeutical method.

According to the present invention, the composition for use in a sequential or simultaneous treatment can be administered intravenously to the patient, under the form of injections, ointment, pulmonary spray; for use in a sequential treatment the composition can also be administered in the following way: the monoclonal antibody is administered intraperitoneally or intravenously while the β-(1,3)-glucan like Laminarin or oligo-β-(1,3)-glucan is administered orally to the patient, under the form of a solution, suspension, syrup, tablet, capsule.

It can also be presented as a bolus, an electuary, or a paste.

Oral formulations of β-(1,3)-glucan like Laminarin or oligo-β-(1,3)-glucan suitable for a sequential treatment in connection with the practice of the present invention include capsules, gels, cachets, tablets, effervescent or non-effervescent powders, tablets, or granules; they may consist of a solution, or suspension in an aqueous or non-aqueous liquid, of an oil-in-water liquid emulsion or of a water-in-oil emulsion.

Generally, the said oral formulations may be prepared by uniformly mixing the active ingredient, i.e. especially, either soluble β-(1,3)-glucan like Laminarin or oligo-β-(1,3)-glucan, eventually together with a chemotherapeutic agent, with liquid carriers or finely divided solid carriers or both, and then if necessary by shaping the product.

Suitable solid carriers comprise lactose, sucrose, gelatin, agar and bulk powders.

Suitable liquid carriers include water, pharmaceutically acceptable fats and oils, alcohols or other organic solvents, including esters, emulsions, syrups or elixirs, suspensions, solutions and/or suspensions, and solutions and or suspensions reconstituted from non-effervescent granules and effervescent preparations reconstituted from effervescent granules.

They also may contain, for example, preservatives, emulsifying agents, suspending agents, diluents, sweeteners, thickeners, and melting agents; preferred liquid carriers are edible oils, for example, corn or canola oils, as well as, polyethylene glycols (PEG).

The therapeutical forms, intended for oral administration, may comprise a non-toxic, pharmaceutically acceptable, inert carrier selected from the group comprising lactose, starch, sucrose, glucose, methyl cellulose, magnesium stearate, dicalcium phosphate, calcium sulfate, mannitol, sorbitol, cyclodextrin, and cyclodextrin derivatives, or the like.

Capsules or tablets containing either β-(1,3)-glucan like Laminarin or an oligo-β-(1,3)-glucan according to the invention should preferably be easily formulated and made easy to swallow or to chew. Tablets may contain suitable carriers, binders, lubricants, diluents, disintegrating agents, coloring agents, flavoring agents, flow-inducing agents, or melting agents. A tablet may be produced by compression or molding, optionally with one or more classical additional ingredients.

Compressed tablets may be prepared by compressing the active ingredient in a free flowing form (e.g., powder, granules) optionally mixed with a binder (e.g., gelatin, hydroxypropylmethylcellulose), lubricant, inert diluent, preservative, disintegrant (e.g., sodium starch glycolate starch, gelatin, natural sugars such as glucose or beta-lactose, corn sweeteners, natural and synthetic gums such as, sodium alginate, carboxymethylcellulose, polyethylene glycol, waxes, or the like. Lubricants used in these dosage forms include sodium oleate, sodium stearate, magnesium stearate, sodium acetate, sodium chloride, or the like. Disintegrating agents include, for example, starch, methyl cellulose, agar, bentonite, xanthan gum or the like. Molded tablets are made by molding in a suitable machine a mixture of the powdered active ingredient moistened with an inert liquid diluent.

The tablets are optionally coated and may be formulated so as to provide slow-or controlled-release of the active ingredient. Tablets may also optionally be provided with an enteric coating to provide release in parts of the gut other than the stomach.

The following examples are intended to illustrate the invention in particular, to illustrate the synergistic effect of a monoclonal antibody, specifically Herceptin, with Laminarin on the tumor growth.

EXAMPLES

Figure 1:
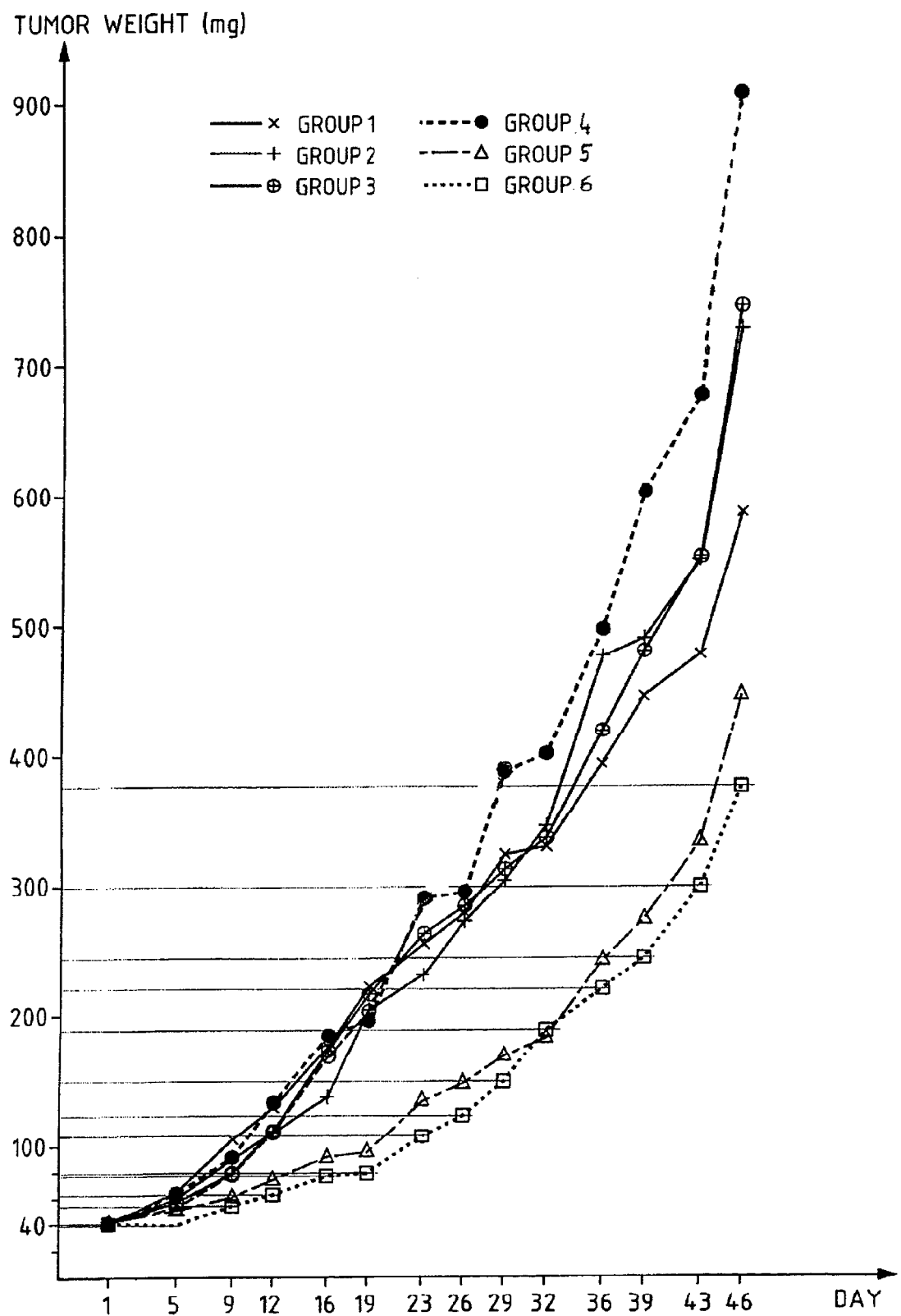
FIG. 1 demonstrates the effect of administration of Pycarine® on tumor growth. Group 1 represents the control. Group 2 represents Herceptin 0.5 mg/kg; Group 3 represents Phycarine® 250 mg/kg; Group 4 represents Phycarine® 250 mg/kg and Herceptin 0.5 mg/kg; Group 5 represents Phycarine® 500 mg/kg and Herceptin 0.5 mg/kg; Group 6 represents Paclitaxel (Mead Johnson) 16 mg/kg.

In the examples, the following products are used:

Phycarine®: Laminarin extracted from brown algae by Laboratoires Goëmar.

Herceptin: manufactured by Genentech.

Example 1

Effect on the Tumor Growth

Female nude mice (nu/nu) between 5 and 6 weeks of age weighing approximately 20 g were obtained from Harlan, Inc. (Madison, Wis.). The BT-474 human breast carcinoma cell line was obtained from the American Type Culture Collection (ATCC). BT-474 was established by E. Lasfargues and W. G. Coutinho from a solid carcinoma of the breast obtained from a 60-year old female patient (2).

Twenty-one-day release 17β-estradiol pellets at 0.25 mg (Innovative Research of America) were implanted subcutaneously into each mouse. The following day, animals were implanted s.c. by trocar with fragments of human tumor carcinomas harvested from s.c. growing tumors in nude mice hosts. When the tumors were approximately 40 mg in size (24 days following inoculation), the animals were pair-matched into treatment and control groups. All of the groups contained 9 mice. All of the animals were ear-tagged and followed individually throughout the experiment.

The mice of each group were administered intra peritoneally with 2 ml of the following composition:

Group 1: (control) sterile $H_2O$, 5 times a day

Group 2: Herceptin 0.5 mg/kg, twice a week during 3 weeks

Group 3: Phycarine® 250 mg/kg, once a day for 5 days

Group 4: Phycarine® 250 mg/kg, once a day for 5 days
Herceptin 0.5 mg/kg, twice a week during 3 weeks Group 5: Phycarine® 500 mg/kg, once a day for 5 days
Herceptin 0.5 mg/kg, twice a week during 3 weeks Group 6: (reference) Paclitaxel (Mead Johnson) 16 mg/kg, once a day for 5 days.

Mice were weighed twice weekly, and tumor measurements were obtained using calipers twice weekly, starting on Day 1. These tumor measurements were converted to mg tumor weight by the standard formula, $(W^2 \times L)/2$ (2). The experiment was terminated when the control group tumor size reached an average of 500 mg. Upon termination (Day 46), the mice were weighed, sacrificed and their tumors were excised. The tumors were weighed, and the mean tumor weight per group was calculated. In this model, the change in mean treated tumor weight/the change in mean control tumor weight×100 was subtracted from 100% to give the tumor growth inhibition (TGI) for each group.

Paclitaxel caused tumor regression in this tumor xenograft model. With this agent, the final weight of a given tumor was subtracted from its own weight at the start of treatment on Day 1. This difference was divided by the initial tumor weight to give the % regression. A mean % tumor regression was calculated from data from mice in a group that experienced tumor regressions.

The results which are expressed as mean value (standard deviation) are given in the following Table 1.

TABLE 1

Average daily weight of the tumor, in mg (standard deviation)

| day | Group 1 | Group 2 | Group 3 | Group 4 | Group 5 | Group 6 |
|---|---|---|---|---|---|---|
| 1 | 40.8 | 40.3 | 40.4 | 40.3 | 40.8 | 40.4 |
|  | (6.0) | (6.3) | (9.8) | (7.3) | (9.2) | (9.8) |
| 5 | 65.0 | 60.0 | 57.1 | 63.8 | 50.8 | 3906 |
|  | (10.2) | (9.4) | (20.4) | (12.1) | (9.9) | (6.7) |
| 9 | 105.7 | 89.9 | 79.5 | 91.4 | 61.0 | 54.2 |
|  | (19.8) | (13.3) | (21.0) | (21.6) | (10.6) | (12.7) |
| 12 | 129.9 | 110.9 | 112.4 | 133.4 | 74.3 | 62.9 |
|  | (18.6) | (17.0) | (31.3) | (32.1) | (18.9) | (16.0) |
| 16 | 175.6 | 137.9 | 172.8 | 184.6 | 91.9 | 77.3 |
|  | (31.2) | (26.7) | (45.8) | (51.8) | (18.6) | (30.2) |
| 19 | 221.8 | 204.6 | 216.5 | 195.4 | 95.4 | 79.4 |
|  | (35.7) | (46.8) | (61.4) | (44.4) | (17.5) | (28.8) |
| 23 | 255.6 | 231.3 | 263.6 | 290.3 | 134.8 | 108.0 |
|  | (48.9) | (46.5) | (68.3) | (77.8) | (30.0) | (42.3) |
| 26 | 279.2 | 272.8 | 284.6 | 295.1 | 148.1 | 123.8 |
|  | (56.8) | (66.4) | (80.6) | (77.9) | (28.1) | (50.3) |
| 29 | 324.1 | 304.7 | 313.0 | 387.4 | 168.6 | 149.5 |
|  | (70.2) | (57.2) | (80.6) | (94.9) | (30.0) | (59.9) |

TABLE 1-continued

Average daily weight of the tumor, in mg (standard deviation)

| day | Group 1 | Group 2 | Group 3 | Group 4 | Group 5 | Group 6 |
|---|---|---|---|---|---|---|
| 32 | 329.9 | 346.0 | 336.5 | 401.7 | 182.8 | 188.8 |
|  | (65.5) | (88.2) | (84.1) | (105.9) | (35.5) | (80.8) |
| 36 | 394.2 | 476.0 | 419.5 | 497.1 | 242.7 | 220.3 |
|  | (86.5) | (139.6) | (108.0) | (121.4) | (47.2) | (91.4) |
| 39 | 445.7 | 489.8 | 479.9 | 602.9 | 274.3 | 244.8 |
|  | (87.7) | (144.5) | (128.4) | (143.5) | (59.1) | (98.5) |
| 43 | 477.6 | 551.1 | 553.1 | 676.4 | 333.4 | 299.6 |
|  | (111.4) | (162.3) | (153.1) | (164.7) | (71.1) | (118.2) |
| 46 | 587.1 | 727.9 | 745.0 | 907.2 | 446.6 | 376.3 |
|  | (124.0) | (193.4) | (186.8) | (216.6) | (104.7) | (150.6) |

The graphical representation was performed utilizing GraphPad Prism® software and is given on FIG. 1, on which, for each group, the corresponding graph represents the weight of the tumor (in mg) in function of the day (from 1 to 46).

Those results show that:
the administration of Phycarin® 500 mg/kg does not allow a limitation of the tumor growth, but on the contrary enhances the growth of the tumor;
the administration of Herceptin 0.5 mg/kg allows a limitation of the growth of the tumor;
the administration of Phycarine® 250 mg/kg allows a limitation of the growth of the tumor which is about the same as the one obtained by administering Herceptin 0.5 mg/kg;
the administration of Phycarine® 500 mg/kg and Herceptin 0.5 mg/kg allows a limitation in the increase of the tumor weight which is far higher than the mean value obtained when administering Herceptin 0.5 mg/kg and Phycarine® 500 mg/kg alone; said activity on the tumor weight being even equivalent to the one obtained when administering a conventional dosage of taxol.

What is claimed is:

1. A therapeutical method comprising administration of a composition comprising a monoclonal antibody with an oligo-β-(1,3)-glucan and a pharmaceutically acceptable carrier, to a human being or to a warm blooded animal suffering from breast cancer in an amount which is effective to treat the breast cancer, wherein the monoclonal antibody is any monoclonal antibody specific to molecular determinants present on breast cancer cells and simultaneously able to activate complement.

2. The method according to claim 1, wherein the oligo-β-(1,3)-glucan is a compound presenting the following formula (1):

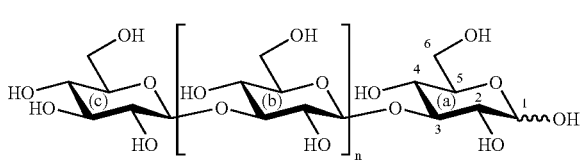

in which n=1 to 10,
or a pharmaceutical acceptable salt thereof.

3. The method according to claim 1, wherein the monoclonal antibody and an oligo-β-(1,3)-glucan are administered simultaneously, sequentially or successively.

4. The method according to claim 1, wherein the composition for use in a successive, sequential or simultaneous treatment can be administered intravenously or intraperitoneally to the patient, under the form of injections, ointment, pulmonary spray; and the composition for use in a sequential treatment can also be administered in the following way: the monoclonal antibody is administered intravenously while the oligo-β-(1,3)-glucan is administered orally to the patient, under the form of a solution, suspension, syrup, tablet, capsule.

5. The method according to claim 1, wherein the effective amount of oligo-β-(1,3)-glucan is 2 to 20 mg/kg when administered orally.

6. A pharmaceutical composition under the form of an injection, ointment, pulmonary spray comprising a therapeutically effective amount of a monoclonal antibody and an oligo-β-(1,3)-glucan or formula (1)

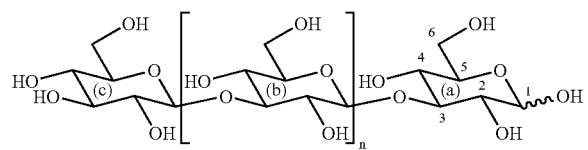

in which n=1 to 10, or a salt pharmaceutically acceptable salt thereof, and a pharmaceutical acceptable carrier, said composition being free of any other glucan.

7. A pharmaceutical composition according to claim 6, further comprising a chemotherapeutic agent.

8. The method according to claim 1, wherein the oligo-β-(1,3)-glucan is a compound presenting the following formula (1):

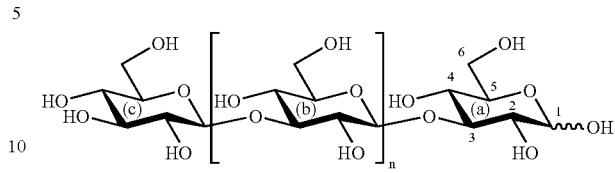

in which n=2 or 3, or a pharmaceutical acceptable salt thereof.

9. A pharmaceutical composition under the form of an injection, ointment, pulmonary spray comprising a therapeutically effective amount of a monoclonal antibody and an oligo-β-(1,3)-glucan or formula (1)

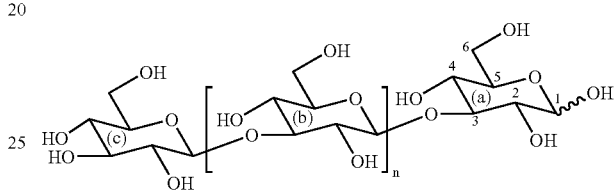

in which n=2 or n=3, or a salt pharmaceutically acceptable salt thereof, and a pharmaceutical acceptable carrier, said composition being free of any other glucan.

* * * * *